US00PP08112P

United States Patent [19]

Dehan

[11] Patent Number: Plant 8,112

[45] Date of Patent: Jan. 19, 1993

[54] IMPATIENS PLANT NAMED FLAMENCO

[75] Inventor: Klara Dehan, Holon, Israel

[73] Assignee: Danziger - "Dan" Flower Farm, Post Beit Dagan, Israel

[21] Appl. No.: 730,611

[22] Filed: Jul. 16, 1991

[51] Int. Cl.[5] ..... A01H 5/00

[52] U.S. Cl. ..... Plt./87.6

[58] Field of Search ..... Plt./87.6

*Primary Examiner*—James R. Feyrer

*Attorney, Agent, or Firm*—Foley & Lardner

[57] ABSTRACT

A new cultivar of Impatiens plant named Flamenco characterized by its compact growth habit, excellent branching, fleshy medium green leaves, and light purple-violet very large flowers.

1 Drawing Sheet

The present invention comprises a new and distinctive cultivar of Impatiens plant, botanically known as Impatiens, and known by the cultivar name Flamenco. Flamenco was developed by me through controlled breeding by crossing the cultivar identified by breeding number 47-11-A as the seed parent with the cultivar designated 0-14-A as the pollen parent.

Asexual reproduction of Flamenco by terminal or stem cuttings taken by applicant at Mishmar Hashiva, Israel has shown that the unique features of this new Impatiens are stabilized and are reproduced true to type in successive propagations.

The following characteristics distinguish the new Impatiens from both its parent varieties and other cultivated Impatients of this type known and used in the fluoriculture industry:

1. Compact growth habit, with excellent branching.
2. Unique leaf structure.
3. Leaves are medium green in color.
4. Flower color is a unique light purple-violet.
5. The flowers are very large, reaching a diameter of approximately 7.5 cm.
6. The stems are given in color.

The accompanying color photographs illustrate the overall appearance and flower detail of this cultivar, showing the colors as true as it is reasonably possible to obtain in a colored reproduction of this type.

The top photo is a top perspective view of the cultivar, and the bottom photo is an enlarged showing of a single flower.

The following is a detailed description of my new Impatients cultivar based on plants produced under commercial practice in Mishmar Hashiva, Israel. The description was made in the winter and in the early spring.

Color references are made to The Royal Horticultural Society Colour Chart except where general terms of ordinary dictionary significance are used.

Parentage:

*Male parent.*—0-14-A.

*Female parent.*—47-11-A.

Propagation.

A. *Type cutting.*—Leaves with axillary buds but not flower buds.

B. *Time to initiate roots.*—8-10 days both at 25°-30° C. summer, and 20°-22° C. winter.

C. *Rooting habit.*—Very good root initiation.

Plant description:

A. *Form.*—Compact, symmetrically mounded, medium size plant with medium green foliage.

B. *Habit of growth.*—Compact plant, good branching.

C. *Foliage description.*—Medium to dark green foliage and medium size leaves. The leaf structure is unique with respect to other known cultivars in that the leaves are fleshier. The fleshiness results in better water retention therefore giving the variety better resistance to water deficiencies. (1) Size: Approximately 10 cm long and 4.5 cm wide at the widest point. (2) Shape: Oval. (3) Texture: Slightly hairy on upper side. (4) Color: Young foliage top side 147A; under side 147B. Mature foliage top side 139A; under side 147B. (5) Venation: Light green.

Flowering description:

A. *Flowering habits.*—Very floriferous, with total inflorescence at any one time forming an extensive canopy due to size of flowers.

B. *Natural flowering season.*—Natural flowering in the spring in moderate climates. In Israel and other warm climates, it will also flower in the winter.

C. *Flower buds.*—Normal shape and development.

D. *Flowers borne.*—Every branch has about 5-6 buds at different stages on the top, and there are normally 2-3 flowers open at the same time on every branch. Flowering is continuous at temperatures above approximately 10° C. and with at least minimum levels of light.

E. *Quantity of flowers.*—Total inflorescence at any one time is about 25-30 opened flowers which, due to the large diameter of the flowers, provides a large umbrella of blooms.

F. *Petals.*—(1) Shape: Typical. (2) Color: Top side in winter when opening 81C, fading to 81D; under side 81D. (3) Number of petals: Five. (4) Size of flowers: 7.5 cm.

G. *Reproductive organs.*—(1) Stamens: One in number. (a) Anther color: White. (b) Pollen color: White. (2) Pistils: (a) Stigma: Cone shaped; green in color. (b) Style: Green in color. (c) Ovaries: One in number; size 1.5 mm; color light green.

I claim:

1. A new and distinct cultivar of Impatiens named Flamenco, as illustrated and described.

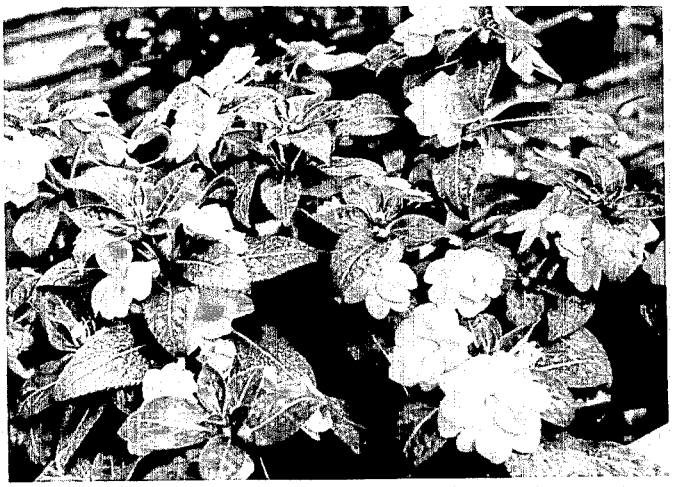
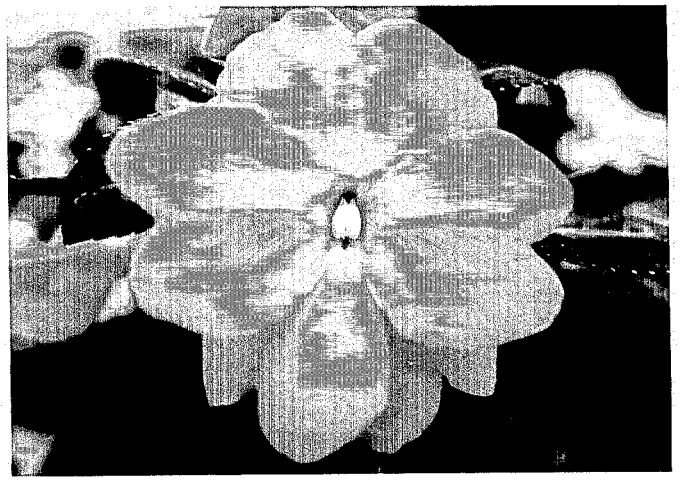

* * * * *